United States Patent [19]

Khera

[11] 3,997,582
[45] Dec. 14, 1976

[54] PROCESS AND CATALYST FOR SYNTHESIZING A GASEOUS HYDROCARBON MIXTURE HAVING A HIGH METHANE CONTENT FROM CARBON MONOXIDE AND HYDROGEN

[75] Inventor: Surjit Singh Khera, Upper Arlington, Ohio

[73] Assignee: Battelle Development Corporation, Columbus, Ohio

[22] Filed: Dec. 8, 1975

[21] Appl. No.: 638,839

[52] U.S. Cl. .................... 260/449.6 M; 48/197 R; 252/466 J; 260/449.6 R
[51] Int. Cl.$^2$ .................... C07C 1/04; C07C 1/16
[58] Field of Search ............. 260/449 M, 449.6 M, 260/449.6 R; 252/466 J; 48/197 R

[56] References Cited
UNITED STATES PATENTS

| | | | |
|---|---|---|---|
| 2,211,022 | 8/1940 | Michael et al. | 260/449.6 |
| 2,231,990 | 2/1941 | Dreyfus | 260/449.6 |
| 2,360,787 | 10/1944 | Murphree et al. | 260/449.6 |

*Primary Examiner*—Howard T. Mars
*Attorney, Agent, or Firm*—Kenneth R. Warburton

[57] ABSTRACT

A gaseous ($C_1$ to $C_4$) hydrocarbon mixture having a high methane content (at least 80 percent by volume on a carbon dioxide-free basis) is obtained by passing a mixture of hydrogen and carbon monoxide at a volume ratio of about 47:53 to 60:40 at a temperature between about 350° and about 450° C. and a pressure of about 200 p.s.i.g. to about 10,000 p.s.i.g. at a volumetric space velocity of about 500 to about 6000 in contact with a sulfur resistant catalyst comprising an interspersed mixture of cobalt oxide, aluminum oxide and zinc oxide. The catalyst comprises about 1 to about 15 weight percent of cobalt oxide, about 15 to 60 weight percent of aluminum oxide and about 35 to about 70 weight percent of zinc oxide. In preparing the catalyst, the cobalt, aluminum and zinc can be separately precipitated as the corresponding hydroxides and then admixed prior to calcination or two or more of such metals can be coprecipitated as the hydroxides at a controlled pH with ammonium hydroxide from the corresponding aqueous nitrate or acetate solutions. The admixed hydroxides of cobalt, aluminum and zinc are then dried and calcined.

8 Claims, No Drawings

PROCESS AND CATALYST FOR SYNTHESIZING A GASEOUS HYDROCARBON MIXTURE HAVING A HIGH METHANE CONTENT FROM CARBON MONOXIDE AND HYDROGEN

This invention relates to a process for catalytically synthesizing a gaseous ($C_1$ to $C_4$) hydrocarbon mixture having a high methane content (at least 80 percent by volume on a carbon dioxide-free basis) from mixtures of carbon monoxide and hydrogen and to a sulfur resistant catalyst for use in the synthesis of said gaseous hydrocarbon mixture.

BACKGROUND OF THE INVENTION

It is well known that there is an increasing shortage of natural gas (chiefly methane) in the United States and there is a generally limited supply of natural gas throughout the world. For this reason, attention is being directed to a substitute or supplement for natural gas. Natural gas suitable for distribution to residential, commercial and industrial consumers is characterized by heating values ranging from about 900 to about 1100 B.t.u./s.c.f. and by a high methane content, normally 80 percent by volume or greater. Such natural gas often contains a small amount of ethane and propane. Therefore, in order to provide a suitable substitute or supplement for natural gas, such substitute or supplement gas should consist essentially of methane or a gaseous hydrocarbon mixture having a high methane content with only small amounts of ethane and propane.

The synthesis of hydrocarbons by hydrogenating carbon monoxide is not a new concept. In fact, the synthesis of methane by hydrogenating carbon monoxide was first described by P. Sabatier and J. B. Senderens in 1902 (Compt. Rend. 134, 514 and 689 [1902]). Higher boiling hydrocarbons were obtained from carbon monoxide and hydrogen in the early 1920's by F. Fischer and H. Tropsch (Chem. Ber. 56, 2428 [1923]). While, at the present time, processes are available for producing a full range of hydrocarbons by hydrogenating carbon monoxide, the economics of such processes has mitigated against their wide-spread commercialization. The products obtained in the catalytic hydrogenation of carbon monoxide can be one or more materials selected from hydrocarbons, alcohols, aldehydes, ketones, esters and fatty acids of almost any chain length, degree of saturation and structure. The relative extent to which one or more of these products is obtained can be controlled to some extent by the selection of the catalyst composition and operating conditions. Catalysts which heretofore have been of special interest in the synthesis of organic compounds from carbon monoxide and hydrogen are those wherein the metal component is selected from iron, cobalt, nickel, ruthenium, zinc and thorium. The behavior of these catalysts in hydrogenating carbon monoxide is dependent to a large extent upon the presence of chemical and structural promotors, upon the method used in preparing the catalyst, upon the catalyst surface conditions, upon the reaction conditions and upon the nature or make-up of the feed gas mixture, i.e., synthesis gas charged to the reaction system.

Nickel has been used as a catalyst for the synthesis of methane according to the reaction $$CO + 3H_2 \rightleftharpoons CH_4 + H_2O \qquad (1)$$

which proceeds from left to right at temperatures below about 500° C. and in the opposite direction at higher temperatures.

Cobalt admixed with thorium dioxide and magnesium oxide, as promotors, and kieselguhr, as a carrier, has been used as a catalyst for the synthesis of higher aliphatic hydrocarbons. (F. Fischer and H. Tropsch, Brennstoff-Chem. 7, 97 [1926]; and F. Fischer and H. Pichler, Brennstoff-Chem. 20, 41, 221 and 247 [1939]).

Iron has been used as a catalyst for the synthesis of aliphatic and aromatic hydrocarbons. In the past, alkali has been used as a promotor when the catalyst contains iron. The alkali is reported to influence surface conditions of the catalyst and to enhance the production of higher molecular weight products. In the early work conducted by F. Fischer and H. Tropsch, alkali-promoted iron-copper catalysts were employed in producing high boiling (gasoline range) hydrocarbons. (F. Fischer and H. Tropsch, Brennstoff-Chem. 9, 21 [1928]). The promoting effect of alkali to iron catalysts was believed to be the result of the formation in its presence of ferric oxide ($Fe_2O_3$) and the prevention of its transition to the less active magnetic iron oxide ($Fe_3O_4$). (G. LeClerc, Compt. Rend 207, 1099 [1939]).

In accordance with the present invention, the presence of alkali in the catalyst is kept at a minimum since it is believed that the presence of alkali in the catalyst of the invention causes the catalyst to fuse and thus materially decrease the surface available for catalytic purposes.

Sintered iron catalysts have previously been used in preparing branched-chain paraffins. These catalysts have been prepared by reducing precipitated iron-alumina catalysts at 1550° F. (British Pat. No. 473,932 [1937]; British Pat. No. 474,448 [1937]; and British Pat. No. 496,880 [1938]).

Ruthenium and ruthenium-containing catalysts have been used in the synthesis of high-melting waxes from hydrogen and carbon monoxide (H. Pichler, Brennstoff-Chem. 19, 226 [1936]; H. Pichler and H. Buffleb, Brennstoff-Chem. 21, 257, 273 and 285 [1940]). Other Group VIII metals, i.e., rhodium, palladium, osmium, iridium and platinum have been less satisfactory than ruthenium (U.S. Pat. No. 1,628,190 [1927]). The effect of pressure upon the yield and type of products with ruthenium catalysts is very pronounced.

Zinc oxide and mixtures of zinc oxide with chromic oxide have been used as catalysts for synthesizing methanol from hydrogen and carbon monoxide at temperatures above 300° C. and pressures above 200 atmospheres. (H. Pichler, Brennstoff-Chem. 33, 289 [1952]).

Oxide catalysts, in general, show a smaller degree of activity toward carbon monoxide plus hydrogen than the metal catalysts. On the other hand, metal catalysts, e.g., nickel, cobalt, iron and ruthenium, are more sensitive to sulfur and sulfur compounds than oxide catalysts.

Prior processes for hydrogenating carbon monoxide to methane and other low boiling hydrocarbons have required hydrogen to carbon monoxide ratios in the order of about 3:1 (see equation 1 hereinabove). Therefore, in many instances, it has been necessary to increase the hydrogen content of synthesis gas by the so-called water gas shift reaction, i.e., $$CO + H_2O \rightarrow CO_2 + H_2 \qquad (2)$$

The carbon dioxide formed in the water gas shift reaction is then removed by compressing the gas and scrubbing it with water or by reacting it with ethanolamines. The hydrogen thus obtained is used according to prior processes to increase the hydrogen to carbon monoxide ratio in synthesis gas to an amount of about 2:1 to 3:1, preferably the latter, i.e., about 3:1.

Coal has been used in the production of synthetic or substitute natural gas (SNG) comprising low boiling hydrocarbons according to the Lurgi process as described by Paul F. H. Rudolph in Chemical Age of India, 25, 289–299 (1974). In the Lurgi process for producing SNG from coal, five separate steps are required: (1) pressure gasification of coal to recover gaseous products and remove ash and tar; (2) crude gas shift conversion wherein steam is reacted with some carbon monoxide to form carbon dioxide and hydrogen, the latter being used to increase the hydrogen to carbon monoxide ratio in the synthesis gas; (3) Rectisol gas purification wherein organic solvents remove impurities from the gas; (4) methane synthesis where the carbon monoxide and hydrogen are reacted to produce methane; and (5) a Phenolsolvan process for treating the gas liquor from coal gasification to remove water-soluble components, e.g., phenols, ammonia and fatty acids.

In accordance with the present invention, a sulfur resistant catalyst is provided for the hydrogenation of carbon monoxide to a gaseous hydrocarbon mixture having a high methane content (at least 80 percent by volume methane on a carbon dioxide-free basis) wherein the $H_2$:CO ratio can be 1:1. Since this ratio is frequently obtained when coal is subjected to complete gasification, there is no need in the process of the present invention to employ a water gas shift reaction such as that used in the Lurgi process. While coal is an economic source of synthesis gas for use as feed gas in the process of the present invention, the synthesis gas can be obtained from any carbonaceous material which can be decomposed to hydrogen and carbon monoxide. Examples of such materials are fossil fuels such as natural gas, bituminous coal, lignite, oil shale, crude oil and residual fuel oils. For the most part, synthesis gas has been obtained from natural gas or coal. The theoretical ideal synthesis gas reaction may be represented as follows:

$$C + H_2O \rightarrow CO + H_2 \qquad (3)$$

One of the impurities frequently present in synthesis gas obtained in the gasification of coal is sulfur or compounds of sulfur. As indicated hereinabove, metal catalysts such as nickel, cobalt, iron and ruthenium are poisoned by sulfur and sulfur compounds. Thus, synthesis gas containing sulfur or sulfur compounds has previously been subjected to a desulfurization process prior to being converted into hydrocarbons. One such process is the Girbitol process as described by C. B. Ames, Mines Magazine 32, 508 (1942). Other desulfurization processes include (1) the iron oxide process (C. C. Hall and A. R. Powell, Office of Technical Services Report No. PB288, Department of Commerce, Washington, D.C.); (2) the "Alkazid Process" (Lorenzen Gerhard and Leithe, Gas and Wasserfach 86, 313 [1943]) in which an alkaline organic compound absorbs hydrogen sulfide and then is steam-stripped for reuse (H. A. Schade, E. Foran and R. C. Aldrich, Office of Technical Services Report No. PB373, Department of Commerce, Washington, D.C.); and (3) F. Fischer and H. Tropsch desulfurization by catalytic reduction of sulfur compounds to hydrogen sulfide (British Pat. No. 254,288 [1925]; British Pat. No. 282,634 [1926]; Canadian Pat. No. 266,382 [1926]; and German Pat. No. 558,558 [1926]).

A process for decomposing organic sulfur compounds to hydrogen sulfide by passing the gas at a temperature above 300° C. over a mixture of alkali metal carbonates and iron oxide is disclosed by Studien and Verwertungs G. m. b. H. in British Pat. No. 469,933 (1937) and German Pat. No. 651,462 (1937). In still another process I. G. Farbenindustrie A.-G. has disclosed a process for decomposing organic sulfur compounds to hydrogen sulfide simultaneously with the water gas shift reaction (U.S. Pat. No. 1,695,130 [1928].

SUMMARY OF THE INVENTION

In accordance with the present invention a catalyst is provided which is resistant to poisoning by sulfur or compounds of sulfur present in products of coal gasification. Thus, the present invention does not require total desulfurization of the synthesis gas obtained in coal gasification prior to being catalytically converted to a gaseous hydrocarbon mixture having a high methane content.

The product with which the present invention is concerned is a gaseous $C_1$ to $C_4$ hydrocarbon mixture having a high methane content. The methane-rich gas when freed of carbon dioxide is characterized by a heating value of about 950 to about 1,000 B.t.u./s.c.f. The carbon dioxide-freed product can be fed directly to a pipeline for use as such. The gaseous $C_1$ to $C_4$ hydrocarbon mixture consists of about 80 to about 100 percent by volume of methane on a carbon dioxide-free basis. Minor amounts of higher hydrocarbon gases, i.e., ethane and propane also may be present. In a few instances, a very minor, yet detectable, amount of butane may be present. The gaseous $C_1$ to $C_4$ hydrocarbons are desirable fuel gases per se or they may be used for gas enrichment. They also may be separated into their individual constituents and used as intermediates in forming other organic compounds. Methane is widely used to upgrade manufactured gas. Ethane can be used in the production of ethylene. It also is useful in the production of ethylene. It also is useful in the production of acetic acid, acetaldehyde, ethyl chloride and nitroethane. Propane is widely used as a fuel in liquified petroleum gas (LPG). It is also used as a refrigerant in chemical, petroleum refining and gas processing operations. Still further, it is useful as a solvent and for injection into subterranean formations to increase the production of crude oil from oil wells. Essentially, the present invention comprises a process for synthesizing a gaseous hydrocarbon mixture having a methane content of at least about 80 percent by volume on a carbon dioxide-free basis from carbon monoxide and hydrogen. The process utilizes a novel sulfur resistant catalyst comprising an interspersed mixture of cobalt oxide, aluminum oxide and zinc oxide. According to the process, a synthesis gas comprising a mixture of hydrogen and carbon monoxide having a volume ratio of about 47:53 to 60:40, preferably a molar ratio of 1:1, is passed through a reaction zone at a temperature of about 350° to about 450° C. and a pressure of about 200 p.s.i.g. to about 10,000 p.s.i.g. or higher, e.g., 25,000 p.s.i.g., at a space velocity (volume of gas per hour per volume of catalyst) of about 500 to about 6000 in contact with a catalyst comprising an interspersed mixture of cobalt oxide, aluminum oxide and zinc oxide. A gaseous hydrocarbon mixture consisting predominantly of methane is recovered from the reaction product. The preferred temperature range is about 375° to about 425° C.; the preferred pressure range is about 200 to about 3000 p.s.i.g.; and the preferred space velocity is about 1000 to about 2000. Optimum values of temperature and pressure may vary according to the composition of the feed gas, type and amount of catalyst, throughout velocity and the like.

DETAILED DESCRIPTION OF THE INVENTION

The feed gas (synthesis gas) employed in the process of the invention may be obtained from a variety of carbonaceous materials. From an economic standpoint, it is preferred to use a low cost material such as bituminous coal, lignite, oil shale and low grade crude and residual fuel oils. Since sulfur is undesirable in pipeline gas, it is preferred to use a synthesis gas source material which contains little or no sulfur when preparing a pipeline gas. While sulfur can be removed from the pipeline gas prior to distribution, the purification step adds to the overall cost and may offset the advantage of using a low cost material in the first instance. The removal of sulfur, however, is not necessary insofar as the catalyst of the invention is concerned since the catalyst is not poisoned by sulfur. The synthesis gas is advantageously obtained by gasification of a low cost coal with steam. As indicated above, however, the process of the invention is not limited to the use of synthesis gas derived from coal but is applicable to mixtures of hydrogen and carbon monoxide, with or without other gaseous ingredients from any source. The presence of carbon dioxide in the synthesis gas has no deleterious affect on methanation. For methanation, the synthesis gas should contain hydrogen and carbon monoxide in a volume ratio of 47:53 to 60:40, preferably a molar ratio of 1:1 since the primary reaction is

$$2CO + 2H_2 \rightarrow CH_4 + CO_2 \qquad (4)$$

The carbon dioxide obtained according to equation (4) is advantageously recycled to a gasifier to obtain improved carbon utilization. There is no water or, if any, only small amounts of water formed when a catalyst of the invention is used in the preferred process of the invention to produce a gaseous hydrocarbon mixture having a high methane content.

The catalyst of the present invention comprises an interspersed mixture of cobalt oxide, aluminum oxide and zinc oxide which mixture by elemental analysis contains less than about 0.5 weight percent, preferably less than about 0.1 weight percent of alkali metal. While care is taken to avoid the use of alkali metals in forming the oxides of cobalt, aluminum and zinc, a small amount, usually less than about 0.1 percent, of alkali metal may appear in the catalyst as a result of impurities in some of the starting materials. The proportion of cobalt oxide in the catalyst comprises about 1 to about 15 weight percent of the catalyst, preferably about 2 to about 10 weight percent. The proportion of aluminum oxide in the catalyst comprises about 15 to about 60 weight percent of the catalyst, preferably about 25 to about 50 weight percent. The proportion of zinc oxide in the catalyst comprises about 35 to about 70 weight percent of the catalyst, preferably about 50 to about 65 weight percent.

The employed catalyst, i.e. dried and/or calcined as well as that optionally subjected to a reduction step prior to usage, is an interspersed mixture of cobalt, aluminum and zinc oxides in the foregoing proportions. For teaching of the invention, the oxide of cobalt in this interspersed mixture also is referred to as "cobalt oxide." By cobalt oxide there is intended to mean each of and any mixture thereof of cobaltous oxide (CoO), cobaltic oxide ($Co_2O_3$), and cobalto-cobaltic oxide ($Co_3O_4$) also sometimes called cobaltosic oxide, in that which to all that are present in the employed catalytic interspersed mixture depends upon the specific drying, calcination and reduction treatments and conditions to which the precipitated hydroxides are subjected prior to usage as employed catalyst.

Even though each of the constituents in the catalyst of the present invention has been used in prior catalysts for hydrogenating carbon monoxide, I know of no catalyst consisting of a combination consisting of an interspersed mixture of cobalt oxide, aluminum oxide and zinc oxide which is used in synthesizing a gaseous mixture of $C_1$ to $C_4$ hydrocarbons having a high methane content from a mixture of hydrogen and carbon monoxide at a molar ratio of about 1:1.

The catalyst of the invention can be prepared by any one of several methods so long as by elemental analysis it contains less than about 0.5 weight percent of alkali metal. The oxides of cobalt, aluminum and zinc can be separately prepared and then admixed with each other or any two or all three of such metal oxides can be formed in the presence of each other. Thus, the catalyst can be prepared by precipitating the metals from aqueous solutions thereof with a non-alkali metal electrolyte, then calcined and admixed or the precipitates can be admixed and then calcined. More specifically, the catalyst can be prepared by separately precipitating the hydroxides of cobalt, aluminum and zinc with ammonium hydroxide from the corresponding nitrates or acetates of such metals. The hydroxides can then be admixed, dried and calcined to form an interspersed mixture of the oxides of cobalt, aluminum and zinc. Alternatively, the hydroxides can be dried, then admixed and calcined. A further modification comprises drying the hydroxides, followed by calcining and then admixing the calcined products. In a preferred embodiment of the invention, the hydroxides of cobalt, aluminum and zinc are precipitated separately from aqueous solutions of cobaltous nitrate, aluminum nitrate and zinc acetate using ammonium hydroxide. Cobaltous hydroxide is precipitated at a pH of 9. Aluminum hydroxide is precipitated at a pH of 6. Zinc hydroxide is precipitated at a pH of 6.5. The three separately precipitated hydroxides are then admixed and subsequently dried at 110° C. The dried catalyst mixture is then treated at 400° C. for a short time, e.g., about 10 minutes with a flowing stream of hydrogen.

Catalyst preparation is conducted under controlled conditions: generally a temperature of about 20° to about 95° C.; although when precipitating zinc hydroxide temperatures up to close to boiling are useful; a maintaining of the pH of the solution at a value within the range of about 6.0 to about 7.5 when coprecipitating any combination of the hydroxides of cobalt, aluminum and zinc, and when separately precipitating the aluminum and zinc hydroxides; and a maintaining of the pH of the solution at a value within the range of about 8.5 to about 9.5 when separately precipitating cobalt hydroxide. If the pH is not maintained as just taught, the resulting catalyst is less effective in the formation of gaseous hydrocarbons. To achieve this pH control, it may be necessary to add ammonia or similar substance, but not alkali, into the solution (suspension). Alkali is undesirable since it causes fusion of the catalyst. The pH is kept at a constant value, preferably through control by a pH meter. In a preferred embodiment of the invention, cobalt, aluminum and zinc are precipitated separately as their hydroxides, preferably with ammonium hydroxide under controlled temperature conditions within the range of about 20° to about 95° C, i.e. of about 90° to 95° C. for cobaltous hydroxide and 20° to 30° C. for aluminum hydroxide and zinc hydroxide while maintaining the pH of the solutions at a value within the range of about 9.5, i.e., pH's of 6 to 7.5 for aluminum hydroxide and zinc hydroxide and a pH of 8.5 to 9.5 for cobaltous hydroxide. The cobalt, aluminum and zinc hydroxides are then admixed with each other. The mixed hydroxides are then dried and calcined generally in the presence of air or oxygen.

Drying may be effected under relatively mild conditions, e.g., 8 to 12 hours at 100° to 120° C. Drying can amount to calcination so long as precipitated hydroxides convert to their oxides and the dried mixture is friable. Alternatively to such concurrent drying and calcination, one may calcinate, after drying, at higher temperatures, for example, at 300° to 400° C. for 2 to 12 hours to obtain a calcined catalyst in the form of interspersed mixed oxides.

The dried catalyst, in which the mixed oxides are interspersed, optionally can be subjected to a reduction step prior to use. Such reduction step can amount to calcination. Reduction can be effected by heating the catalyst composition in the presence of hydrogen at an elevated temperature, normally at a temperature of about 300° to 400° C. The hydrogen treatment or preactivation may change the oxidation state of the metals present or it may reduce at least a portion of the oxides to lower oxides and/or to their metallic state. Depending upon the degree of reduction, a dried or dried and calcined catalyst may be treated with hydrogen at a temperature of about 300° to 450° C. for a period of 5 minutes to 48 hours. The catalyst may be formed into any desired shape such as, for example, granules, pills, pellets and the like.

It has been found that the use of a catalyst of the invention is particularly effective in the synthesis of gaseous hydrocarbons from mixtures of hydrogen and carbon monoxide obtained in the gasification of coal in the presence of sulfur compounds, such as hydrogen sulfide and mercaptans, since the catalyst of the invention is not poisoned by sulfur compounds. By contrast, conventional iron and nickel catalysts are rapidly poisoned by the presence of sulfur compounds necessitating extensive gas purification facilities to maintain catalyst activity. These facilities may not be required when a catalyst of the invention is employed. Thus, the cost of producing fuel gas according to the process of the invention is substantially lower than the cost of producing fuel gas with conventional iron and nickel catalysts. In accordance with the present invention, coal may be gasified by reaction with steam at about 1,000 to 6,000 p.s.i.g. and at an elevated temperature of about 800° C. The product of such a reaction typically contains $H_2$, $CH_4$, $C_2H_6$, CO, $CO_2$ and some sulfur or sulfur-containing compounds. After removing the $CH_4$ and $C_2H_6$, the remaining gas can be subjected to the process of the present invention.

The process of the invention can be operated as a multistage or single stage process in either a fixed-bed or moving-bed reactor. Preferably, however, a recycle system, in which unconverted hydrogen and carbon monoxide are recycled to the reactor, is used. In any process according to the invention, temperature and pressure control in or between synthesis converters can be any suitable means such as, for example, feed gas preheaters, coolers, quenchers, compressors and the like.

The reaction of hydrogen with carbon monoxide in volume ratios of 47:53 to 60:40 and preferably a molar ratio of about 1:1 to produce a gaseous ($C_1$ to $C_4$) hydrocarbon mixture having a high methane content is conducted at a temperature of about 350° to about 450° C., preferably about 375° to about 425° C., a space velocity (volume of gas per hour per volume of catalyst) of about 500 to about 6000, preferably about 1000 to about 2000, and a pressure of about 200 to about 10,000 p.s.i.g., preferably about 200 to about 3000 p.s.i.g., in the presence of an interspersed mixture of cobalt oxide, aluminum oxide and zinc oxide which mixture by elemental analysis contains an alkali content of less than 0.5 percent, based on the weight of the catalyst, and preferably less than 0.1 weight percent. The space velocity will depend to some extent upon the type of reaction system used. For fixed-bed reactors, the number of volumes of gas per volume of catalyst per hour, can be about 500 to about 6000 and is preferably about 1000 to about 2000; for fluidized-bed operation using recycle, the total feed space velocity is much higher and may be about 3000 to about 5000.

The invention is further illustrated by reference to the following examples which are intended to be representative rather than restrictive of the scope of the invention.

EXAMPLE I

Preparation of catalyst

In this example, the hydroxides of cobalt, aluminum and zinc are precipitated separately and then admixed prior to drying according to the procedure which follows.

An aqueous solution of zinc acetate is prepared by dissolving 33.72 gms of zinc acetate in 1000 ml of distilled and demineralized water in a 3000 ml beaker. Ammonium hydroxide is added slowly with stirring to the aqueous solution of zinc acetate at room temperature until the pH of the solution is 6.5. In this disclosure, including the examples, there is intended by "room temperature" to mean a temperature of 20° to 25° C. (about 68° to 77° F). The pH is continuously measured while adding the ammonium hydroxide. The precipitate thus formed comprising zinc hydroxide is separated from the reaction mass by filtration. The filter cake is then placed in a 500 ml beaker (A).

An aqueous solution of aluminum nitrate is prepared by dissolving 41.40 gms of aluminum nitrate in 1000 ml of distilled and demineralized water in a 3000 ml beaker. Ammonium hydroxide is added slowly with stirring to the aqueous solution of aluminum nitrate at room temperature until the pH of the solution is 6. The precipitate thus formed comprising aluminum hydroxide is separated from the reaction mass by filtration. The filter cake is admixed with the zinc hydroxide in beaker (A).

An aqueous solution of cobaltous nitrate is prepared by dissolving 6.17 gms of cobaltous nitrate in 400 ml of distilled and demineralized water. Ammonium hydroxide is added slowly with stirring to the aqueous solution of cobaltous nitrate at room temperature until the pH of the solution is 9. The precipitate thus formed (pink color over green precipitate) is stirred for 10 hours whereupon a light brown precipitate is obtained. The precipitate thus formed comprising cobaltous hydroxide is separated from the reaction mass by filtration, washed with 500 ml of distilled water and admixed with the aluminum hydroxide and zinc hydroxide in beaker (A).

The mixture of cobaltous hydroxide, aluminum hydroxide and zinc hydroxide in beaker (A) is stirred at 30° C., for 2 hours. The beaker (A) containing the mixed hydroxides is then placed in an oven to dry at 110° to 120° C. for 12 hours. The dried precipitate has a brown-black color and comprises an interspersed mixture of cobalt oxide, aluminum oxide and zinc oxide in the following weight proportions

| Composition | Weight Percent |
|---|---|
| Cobalt oxide | 6.4 |
| Aluminum oxide | 29.1 |
| Zinc oxide | 64.5 |

The alkali metal content, by elemental analysis, is less than 0.1 weight percent of the mixture.

Test of the catalyst

The catalyst obtained above is evaluated in the synthesis of a gaseous hydrocarbon mixture having a high methane content from a mixture of hydrogen and carbon monoxide in a fixed-bed reactor. In evaluating the catalyst, it is sized by screening through sieves. The catalyst particles which are used are those which pass through a U.S. Mesh No. 12 sieve and are retained on a U.S. Mesh No. 30 sieve.

The reactor consists of a 304 stainless steel tube 18 inches in length with an inside diameter of ¾-inch and an outside diameter of 3 inches. A constant temperature zone in the reactor has a volume of 25 cc. The gas inlet side of the tube is connected to a high pressure rotameter, a flow control needle valve and a pressure regulator. The outlet side of the tube is connected to a pressure condenser surrounded by ice, a flow control needle valve, a dry ice trap and flow indicators.

The synthesis gas used in the evaluation of the catalyst consists of a mixture of hydrogen and carbon monoxide in a volume ratio of 49:51 (molar ratio of hydrogen to carbon monoxide of 1:1.04).

In evaluating the catalyst, the reactor is charged with 10 gms (10.5 cc) of the sieved catalyst. The catalyst is maintained in place by packing each end of the reactor with ⅛-inch fish spine insulators. In starting the test, hydrogen is passed through the system at 1000 p.s.i.g. at a flow rate of 18 liters per hour at room temperature. The temperature of the reactor is then increased to 400° C. over a period of about 35 to 40 minutes. When a temperature of 400° C. is reached, the hydrogen is passed through the system for only another 10 minutes. Hydrogen is then replaced by synthesis gas comprising a mixture of hydrogen and carbon monoxide in a volume ratio of 49:51 (molar ratio of hydrogen to carbon monoxide of 1:1.04). The temperature of the reactor is maintained at 400° C., and 1,000 p.s.i.g. over a period of about 5 hours. Gas samples (2 ml) are obtained at room conditions and analyzed by a 2002 Varian Gas Chromatography Unit. At the end of the evaluation, the catalyst is cooled to room temperature and weighed. An observation is made as to whether any liquids are formed in the traps. In using the catalyst of Example 1, the methane content of the gas is 99.6 percent by volume on a carbon dioxide-free basis. The final weight of the catalyst is 6.92 gms (9 cc). The data obtained in this test are summarized in Table 1.

EXAMPLE 2

Preparation of catalyst

In this example, the procedure and sequence of steps used in preparing the catalyst is the same as that used in Example 1. In this example, however, the amount of zinc acetate used is 33.72 gms; the amount of aluminum nitrate used is 44.16 gms; and the amount of cobaltous nitrate used is 2.46 gms. The catalyst which is obtained comprises an interspersed mixture of cobalt oxide, aluminum oxide and zinc oxide in the following weight proportions.

| Composition | Weight Percent |
|---|---|
| Cobalt oxide | 2.6 |
| Aluminum oxide | 31.7 |
| Zinc oxide | 65.7 |

The alkali metal content, by elemental analysis, is less than 0.1 weight percent of the mixture.

Test of the catalyst

The catalyst is evaluated by the same procedure and in the same test equipment as that used in Example 1. The initial weight of the catalyst used, however, is 11.1 gms having a bulk volume of 10 cc. The final weight of the catalyst is 8.22 gms having a volume of 8 cc. The methane content of the gas obtained is 91.1 percent by volume on a carbon dioxide-free basis. The data obtained in the test are summarized in Table 1.

EXAMPLE 3

Preparation of catalyst

In this example, the hydroxides of cobalt and aluminum are coprecipitated and then admixed with the separately precipitated hydroxide of zinc according to the procedure which follows. The catalyst is not reduced with hydrogen prior to being contacted with synthesis gas.

An aqueous solution of cobaltous nitrate and aluminum nitrate is prepared by dissolving 12.34 gms of cobaltous nitrate and 93.84 gms of aluminum nitrate in 1400 ml of distilled and demineralized water. Ammonium hydroxide is added slowly with stirring to the aqueous solution of cobaltous nitrate and aluminum nitrate at room temperature until the pH of the solution is 6.5. The precipitate (pink) thus formed comprising a mixture of cobaltous hydroxide and aluminum hydroxide is separated from the reaction mass by filtration, washed with 500 ml of distilled water and transferred as a paste to a 400 ml beaker (A).

An aqueous solution of zinc nitrate is prepared by dissolving 36.55 gms of zinc nitrate in 500 ml of distilled and demineralized water. The solution is then heated to its boiling point and stirred. Ammonium hydroxide is added slowly with stirring to the heated solution (90°–95° C.) until the pH of the solution is 7.0. The white precipitate thus formed comprising zinc hydroxide is separated from the reaction mass by filtration, washed with 500 ml of distilled water and transferred to beaker (A) containing the mixed cobaltous hydroxide and aluminum hydroxide. To this mixture of hydroxides in beaker (A) is added 300 ml of distilled water. The mixture is stirred to effect substantial homogenization. The beaker is then placed in an oven at 120° C. for about 12 hours. The interspersed mixture of the dried hydroxides is then calcined by passing air over the catalyst in a furnace at 400° C. for 12 hours. The catalyst thus obtained comprises a sulfur resistant, interspersed mixture of cobalt oxide, aluminum oxide and zinc oxide in the following weight proportions

| Composition | Weight Percent |
|---|---|
| Cobalt oxide | 10 |
| Aluminum oxide | 50 |
| Zinc oxide | 40 |

The alkali metal content, by elemental analysis, is less than 0.1 weight percent of the mixture.

Test of the catalyst

In evaluating the catalyst of this Example 3, the tube reactor is charged with 10 gms (11 cc) of sieved catalyst of a −12 to +30 U.S. Mesh No. sieve size. The catalyst is retained in the reactor as in Example 1 by packing each end of the reactor with ⅛-inch fish spine insulators. The synthesis gas in a mixture of hydrogen and carbon monoxide in a volume ratio of 49:51 (molar ratio of hydrogen to carbon monoxide of 1:1.04). In starting the test, the synthesis gas at 1000 p.s.i.g. is passed through the system and the flow is stabilized at 18 liters per hour at room temperature. The temperature of the reactor is then increased to 400° C. over a period of about 45 minutes. The synthesis gas is passed through the catalyst at a temperature of 400° C. and a pressure of 1000 p.s.i.g. for a period of 6 hours. Gas samples (2 ml) are obtained at room conditions and analyzed by a 2002 Varian Gas Chromatography Unit as in Example 1. The methane content of the gas obtained is 82.6 percent by volume on a carbon dioxide-free basis. The data obtained in the test are summarized in Table 1.

distribution to residential, commercial and industrial consumers. It will be noted further that the volume percent methane is greater when the catalyst is reduced with hydrogen prior to introduction of the synthesis gas.

While my invention has been described above with reference to various specific examples and embodiments, it will be understood that the invention is not limited to such examples and embodiments and may be variously practiced within the scope of the claims hereinafter made.

I claim:

1. A process for the synthesis of a gaseous hydrocarbon mixture having a high methane content comprising:
   a. contacting hydrogen and carbon monoxide in a volume ratio of about 47:53 to about 60:40 at a temperature of about 350° to about 450° C. and a pressure of about 200 to about 10,000 p.s.i.g. at a space velocity of about 500 to about 6000 with a catalyst comprising an interspersed mixture of cobalt oxide, aluminum oxide and zinc oxide which mixture by elemental analysis contains less than about 0.5 weight percent of alkali metal, said catalyst comprising about 1 to about 15 weight percent of cobalt oxide, about 15 to about 60 weight percent of aluminum oxide and about 35 to about 70 weight percent of zinc oxide; and
   b. recovering a gaseous hydrocarbon product of said synthesis comprising a hydrocarbon mixture having a high methane content.

2. A process according to claim 1 wherein the cobalt oxide comprises about 2 to about 10 weight percent of the catalyst, the aluminum oxide comprises about 25 to about 50 weight percent of the catalyst and the zinc oxide comprises about 40 to about 65 weight percent of the catalyst, and which mixture by elemental analysis contains less than 0.1 weight percent of alkali metal.

3. A process according to claim 2 wherein the cobalt oxide comprises about 6.5 weight percent of the catalyst, the aluminum oxide comprises about 29 weight percent of the catalyst and the zinc oxide comprises about 64.5 weight percent of the catalyst.

4. A process according to claim 2 wherein the methane content of the gaseous hydrocarbon mixture is at least 80 percent by volume on a carbon dioxide-free basis.

5. A process for the synthesis of a gaseous hydrocarbon mixture having a high methane content comprising:

Table 1

| Example No. | Catalyst* Composition | | Catalyst Reduction min/° C. | CO Conversion % | S.V. hr⁻¹ | Final Gas : Vol. % | | | | | | Liquids Water ** | Methane Vol. % *** |
|---|---|---|---|---|---|---|---|---|---|---|---|---|---|
| | | | | | | $C_1$ | $C_2$ | $C_3$ | $CO_2$ | $H_2$ | CO | | |
| 1 | CoO | 6.4 | 10/400 | 100 | 1800 | 54.8 | 0.5 | 0.2 | 45.0 | — | — | 3.5 cc t | 98.7 |
| | $Al_2O_3$ | 29.1 | | | | | | | | | | | |
| | ZnO | 64.5 | | | | | | | | | | | |
| 2 | CoO | 2.6 | 10/400 | 93.6 | 1800 | 48.75 | 0.5 | — | 42.5 | 2.0 | 6.25 | 4.5 cc t | 84.8 |
| | $Al_2O_3$ | 31.7 | | | | | | | | | | | |
| | ZnO | 65.7 | | | | | | | | | | | |
| 3 | CoO | 10 | None | 93.6 | 1636 | 47.5 | 0.85 | — | 42.5 | 2.9 | 6.25 | — t | 82.6 |
| | $Al_2O_3$ | 50 | | | | | | | | | | | |
| | ZnO | 40 | | | | | | | | | | | |

*Cobalt oxide is presented as cobaltous oxide (CoO) for convenience in providing weight percent values.
**t = trace, <1 ml water per 4 cu. ft. of feed gas
***Volume percent methane in the final gas on a carbon dioxide-free basis It will be noted from the data in Table 1 that the volume of methane in all examples is above the 80 percent value normally found in natural gas suitable for ing:
   a. contacting hydrogen and carbon monoxide in a volume ratio of about 47:53 to about 60:40 at a temperature of about 350° to about 450° C. and a pressure of about 200 to about 10,000 p.s.i.g. at a space velocity of about 1000 to about 6000 with a catalyst prepared by (1) precipitating cobaltous hydroxide with ammonium hydroxide from an aqueous solution of cobaltous nitrate at a temperature of about 90° to about 95° C. while maintaining the pH of the solution within the range of about 6.0 to about 9.5; (2) recovering the cobaltous hydroxide from "(1)"; (3) precipitating aluminum hydroxide with ammonium hydroxide from an aqueous solution of aluminum nitrate at a temperature of about 20° to about 30° C. while maintaining the pH of the solution within the range of about 6.0 to about 7.5; (4) recovering the aluminum hydroxide from "(3)"; (5) precipitating zinc hydroxide with ammonium hydroxide for an aqueous solution of zinc acetate at a temperature of about 20° to about 30° C. while maintaining the pH of the solution within the range of about 6.0 to about 7.5; (6) recovering the zinc hydroxide from "(5)"; (7) admixing the precipitates of cobaltous hydroxide, aluminum hydroxide and zinc hydroxide; and (8) drying and calcining the mixed hydroxides of cobalt, aluminum and zinc in the presence of air at a temperature of about 100° to about 120° C. to obtain an interspersed mixture of the oxides of cobalt, aluminum and zinc; and b. recovering a gaseous hydrocarbon product of said synthesis comprising a hydrocarbon mixture having a high methane content.

6. A process according to claim 5 wherein the methane content of the gaseous hydrocarbon mixture is at least 80 percent by volume on a carbon dioxide-free basis.

7. A process for the synthesis of a gaseous hydrocarbon mixture having a high methane content comprising:

a. contacting hydrogen and carbon monoxide in a volume ratio of about 47:53 to about 60:40 at a temperature of about 350° to about 450° C. and a pressure of about 200 to about 10,000 p.s.i.g. at a space velocity of about 1000 to about 6000 with a catalyst prepared by (1) precipitating cobaltous hydroxide with ammonium hydroxide from an aqueous solution of cobaltous nitrate at a temperature of about 90° to about 95° C. while maintaining the pH of the solution within the range of about 6.0 to about 9.5; (2) recovering the cobaltous hydroxide from "(1)"; (3) precipitating aluminum hydroxide with ammonium hydroxide from an aqueous solution of aluminum nitrate at a temperature of about 20° to about 30° C. while maintaining the pH of the solution within the range of about 6.0 to about 7.5; (4) recovering the aluminum hydroxide from "(3)"; (5) precipitating zinc hydroxide with ammonium hydroxide from an aqueous solution of zinc acetate at a temperature of about 20° to about 30° C. while maintaining the pH of the solution within the range of about 6.0 to about 7.5; (6) recovering the zinc hydroxide from "(5)"; (7) admixing the precipitates of cobaltous hydroxide, aluminum hydroxide and zinc hydroxide; (8) drying and calcining the mixed hydroxides of cobalt, aluminum and zinc in the presence of air at a temperature of about 100° to about 120° C. to obtain an interspersed mixture of the oxides of cobalt, aluminum and zinc; and (9) preactivating the mixed oxides of cobalt, aluminum and zinc by treating the mixture with hydrogen at a temperature of about 300° to about 400° C. for about 5 minutes to about 48 hours; and b. recovering a gaseous hydrocarbon product of said synthesis comprising a hydrocarbon mixture having a high methane content.

8. A process according to claim 7 wherein the methane content of the gaseous hydrocarbon mixture is at least 80 percent by volume on a carbon dioxide-free basis.

* * * * *